US00PP11593P

United States Patent [19]

Schütze

[11] Patent Number: Plant 11,593

[45] Date of Patent: Oct. 24, 2000

[54] POINSETTIA PLANT NAMED 'FISCOR CANDY'

[75] Inventor: Peter Schütze, Bordesholm, Germany

[73] Assignee: Florfis AG, Binningen, Switzerland

[21] Appl. No.: 09/132,754

[22] Filed: Aug. 12, 1998

[51] Int. Cl.[7] ..... A01H 5/00

[52] U.S. Cl. ..... Plt./303

[58] Field of Search ..... Plt./303, 306, 307, Plt./304

[56] References Cited

U.S. PATENT DOCUMENTS

P.P. 8,733 5/1994 Fruehwirth ..... Plt./303

OTHER PUBLICATIONS

GTITM UPOVROM Citation For 'Fiscor Candy' As Per CA PBR 97–1134; Jan. 20, 1997.

GTITM UPOVROM Citation For 'Fiscor Candy' As Per De PBR EUP 00196; Jan. 20, 1997.

GTITM UPOVROM Citation For 'Fiscor Candy' As Per JP PBR 10772; Mar. 31, 1998.

GTITM UPOVROM Citation For 'Fiscor Candy' As Per QZ PBR 980030; Jan. 8, 1998.

*Primary Examiner*—Howard J. Locker
*Assistant Examiner*—Kent L. Bell
*Attorney, Agent, or Firm*—Foley & Lardner

[57] ABSTRACT

'Fiscor Candy' is characterized by light-salmon main bract color, which is slightly freckled with pink, with the intensity of color increasing from the lower to upper bracts; ovate shaped and only weakly lobed bracts which are in an overlapping arrangement and form a flat inflorescence with hardly any gaps between the bracts; dark-green foliage with weak to distinctly lobed leaves; compact to medium-tall and relatively broad and bushy plant habit; and good keeping quality of bracts as well as foliage.

1 Drawing Sheet

BACKGROUND OF THE INVENTION

The present invention relates to a new and distinct cultivar of Poinsettia plant known by the cultivar name 'Fiscor Candy' and botanically known as *Euphorbia pulcherrima.*

'Fiscor Candy' is a naturally occurring, branch mutation of 'Fiscor' (U.S. Plant Pat. No. 9,364). 'Fiscor' is a cultivar characterized by dark-red bract color, dark-green foliage, medium-tall plant habit and medium-early flowering response.

The mutation was discovered by the inventor Peter Sch ütze, among a group of flowering plants of the parent cultivar growing in his greenhouse in Bordesholm, Germany, in December1995.

One plant had partially developed bracts of a somewhat variable, slightly freckled, salmon-pink color. This plant was taken to Hillscheid, Germany, for further examination. Shoots from the mutated area were used for propagation, and the off-spring were grown under short-day conditions in order to induce flowering. The flowering plants were found to be somewhat variable with respect to the intensity of the bracts color, and therefore were divided into three groups (light-salmon, medium, and relatively intensely pink colored), which were then propagated separately and treated as different clones. After further examination in autumn 1996, the light salmon colored clone proved to be stable and uniform. The first asexual propagation of 'Fiscor Candy' was carried out by stem cuttings in Hillscheid, Germany in 1996.

Horticultural examination initiated in 1996 and continuing thereafter has demonstrated that the combination of characteristics as herein disclosed for 'Fiscor Candy' are firmly fixed and are retained through successive generations of asexual reproduction.

BRIEF DESCRIPTION OF THE INVENTION

The following traits have been repeatedly observed and are determined to be basic characteristics of 'Fiscor Candy' which in combination distinguish this Poinsettia as a new and distinct cultivar:

1. light-salmon main bract color, slightly freckled with pink, with the intensity of color increasing from the lower to the upper bracts;

2. ovate-shaped, only weakly-lobed bracts which are in an overlapping arrangement and form a flat inflorescence with hardly any gaps between the bracts.

3. dark-green foliage with weak to distinctly lobed leaves;

4. compact to medium-tall, relatively broad and bushy plant habit;

5. medium to early flowering response; and 6. good keeping quality of bracts as well as of foliage.

'Fiscor Candy' has not been observed under all possible environmental conditions. The phenotype may vary significantly with variations in environment such as temperature, light intensity, and daylength without, however, any variance in genotype. The following observations, measurements and comparisons describe plants grown in Langley, British Columbia, Canada, under greenhouse conditions which approximate those generally used in commercial practice.

Of the many commercial cultivars known to the inventor, the most similar in comparison to 'Fiscor Candy' are the parent variety 'Fiscor', and the commercial variety '4-91', (U.S. Plant Pat. No. 8,733) European Union varietal designation 'Monet'. Reference is made to Table A, which compares certain characteristics of 'Fiscor Candy' to those same characteristics of '4-91'. The comparison was made in a greenhouse in Langly, British Columbia, Canada in 1997. In comparison to the red-flowering parent variety 'Fiscor', 'Fiscor Candy' has light salmon-pink colored bracts with stems, petioles and veins without anthocyanin coloring. Other morphological characteristics of the cultivars are very close.

In comparison to '4-91', 'Fiscor Candy' has a more salmon or orange, less pink hue of bract color, dark-green foliage, in contrast to the medium green color of '4-91', and less distinctly lobed bracts and leaves. The plant habit of 'Fiscor Candyp' stays lower because of the earlier initiation of flowering compared to '4-91'. As a result, 'Fiscor Candy' can be marketed about 10 to 14 days earlier than '4-91'.

TABLE A

| Characteristic | 'Fiscor Candy' | '4-91' |
|---|---|---|
| Color of foliage | dark-green | medium-green |
| Color of primary bracts upper surface (lower true bracts) | light salmon-pink, RHS 38A to 38B | salmon pink, RHS 39B or lighter |
| Color of secondary bracts upper surface (upper true bracts) | salmon-pink, RHS 48C | rose-red, RHS 52A to 52B |
| Anthers | whitish | pink |
| Pistils | light red stigma | pistils were not developed, none observed |
| Height | 30 cm | about 40 cm |
| Flower response | medium | medium to late |

BRIEF DESCRIPTION OF THE DRAWING

The accompanying color photographic sheet shows typical inflorescences and foliage characteristics of 'Fiscor Candy' with colors being as true as possible with an illustration of this type.

DETAILED BOTANICAL DESCRIPTION

In the following description, color references are made to The Royal Horticultural Society (R.H.S.) Colour Chart, the color values were determined indoors in a north light. The plants described were grown in a greenhouse in Langley, British Columbia, Canada, in autumn 1997. Rooted cuttings were planted into 15 cm pots on August 1, and were pinched 18 days later. The minimum temperature was 20° C. until mid November. The plants developed flowers under natural short-day conditions. Observations and measurements were taken at the beginning of flowering.

Classification:

*Botanical.*—*Euphorbia pulcherrima.*

*Commercial.*—'Fiscor Candy'.

Parentage/orgin: Naturally occurring branch mutation of 'Fiscor'.

Plant description:

*Form.*—Shrub, self-branching, producing a medium number of branches.

*Growth habit.*—Compact to medium-tall, relatively broad and bushy plant habit; branches usually grow at an angle of approximately 45° with respect to the main stem. Height, above soil, is 30.0 cm and width is 50.0–55.0 cm. The average number of branches is 9.

Rooting: Medium, about 24 days.

Blooming habit: Flowering begins under natural short-day conditions in autumn: Botanically, around December 1; commercially, bracts sufficiently colored in late November. The flowering response time is about 9 weeks, depending on temperature.

Foliage:

*Shape.*—Broad ovate, moderately lobed, with rounded or slightly wedge-shaped base, and acuminate tip.

*Texture.*—Smooth, weak veins.

*Margin.*—Entire, apart from the lobes.

*Size.*—Leaf blade length is 13.0 cm; leaf blade width is 8.9 cm; petiole length is 7.0 cm.

*Color.*—Dark green, white-green veining: upper surface is near R.H.S. 139A; under surface is R.H.S. 138A.

*Leaf petiole.*—Light green, no anthocyanin, about R.H.S. 147D.

Flowering description:

*Inflorescence.*—The bracts are borne horizontally, forming a star-shaped ring with a center with hardly any gaps between the bracts, after-sale keeping quality is usually very good.

*Average number of inflorescence.*—7.5; Approximately 90% of the branches develop a complete inflorescence.

*Average number of inflorescence.*—24.0 cm.

*Bracts, shape.*—Ovate to broad elliptical, usually only weak lobes, rounded base and acuminate tip, flat.

*Number.*—Approximately 6–8 true bracts at the beginning of flowering and usually 2 transient or stem bracts that are completely colored. There are 3 primary bracts which are the largest true bracts and form the base of the inflorescence; there are 3–5 secondary bracts.

*Texture.*—Surface smooth or slightly rugose.

*Color.*—Main color is light salmon-pink with tiny pink speckles, stem or transient bracts are very light, almost yellowish in color near R.H.S. 23D, while the intensity of coloration increases with younger bracts, the smallest inner bracts being rose red/carmine red. Upper surface is about R.H.S. 38A to 38B or lighter (larger, lower bracts) and about R.H.S. 48C (smaller, upper bracts). Lower surface is about R.H.S. 29C (larger bracts) and R.H.S. 51B to 51C (smaller bracts).

*Size.*—Largest bract length is 13.6 cm and width is 9.6 cm; petiole is 2.0 cm.

*Postproduction longevity.*—Medium to long; relatively good maintenance indoors. Good quality for marketing is maintained for at least 4 weeks from the beginning of flowering.

*Cyathia, color.*—Light green to medium green, top light pink.

*Diameter of cyathia clustr.*—23.0 mm.

*Borne.*—About 10 in a narrow cluster.

*Retention.*—Medium (5) in a range of 1 to 9, depending on cultivation conditions.

*Nectar cups.*—Medium sized, golden yellow, no anthocyanin.

Reproductive organs:

*Stamens.*—Filaments whitish/yellowish, fertile with yellow pollen.

*Pistils.*—Style light-green to white, stigma light-red.

*Ovaries.*—Triangular, 3-celled, 3 ovules.

*Disease resistance.*—Typical of the species.

I claim:

1. A new and distinct poinsettia plant named 'Fiscor Candy', substantially as illustrated and described.

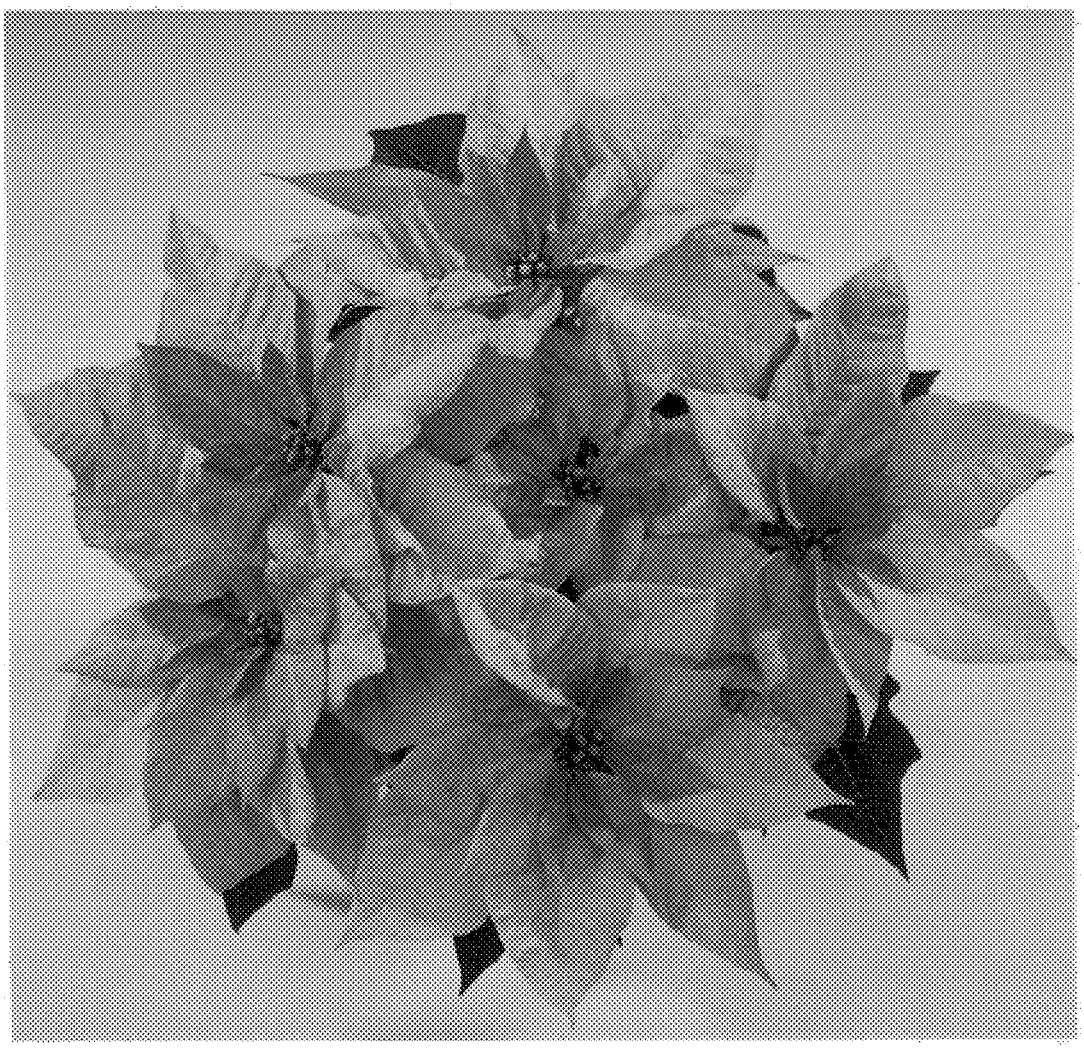

* * * * *